(12) United States Patent
Lorenzo

(10) Patent No.: US 9,034,028 B2
(45) Date of Patent: May 19, 2015

(54) BRAID EXPANSION RING WITH MARKERS

(71) Applicant: DePuy Synthes Products, LLC, Raynham, MA (US)

(72) Inventor: Juan A. Lorenzo, Davie, FL (US)

(73) Assignee: DEPUY SYNTHES PRODUCTS, INC., Rayhnham, MA (US)

( * ) Notice: Subject to any disclaimer, the term of this patent is extended or adjusted under 35 U.S.C. 154(b) by 105 days.

(21) Appl. No.: 13/802,030

(22) Filed: Mar. 13, 2013

(65) Prior Publication Data

US 2014/0277376 A1    Sep. 18, 2014

(51) Int. Cl.
*A61F 2/82*    (2013.01)
*A61F 2/91*    (2013.01)
*A61F 2/86*    (2013.01)

(52) U.S. Cl.
CPC ... *A61F 2/82* (2013.01); *A61F 2/86* (2013.01); *A61F 2/91* (2013.01); *A61F 2250/0098* (2013.01)

(58) Field of Classification Search
CPC ............. A61F 2/82; A61F 2/844; A61F 2/86; A61F 2/88; A61F 2/89; A61F 2/90
USPC ............... 606/191, 198; 623/1.15, 1.16, 1.32, 623/1.34
See application file for complete search history.

(56) References Cited

U.S. PATENT DOCUMENTS

| 5,817,126 | A | 10/1998 | Imran | |
|---|---|---|---|---|
| 2006/0064156 | A1 | 3/2006 | Thistle et al. | |
| 2008/0071307 | A1 | 3/2008 | DeBruyne et al. | |
| 2011/0184508 | A2* | 7/2011 | Burmeister et al. | 623/1.19 |
| 2011/0264186 | A1 | 10/2011 | Berglung | |
| 2012/0016464 | A1* | 1/2012 | Seguin | 623/1.26 |
| 2012/0041538 | A1* | 2/2012 | White et al. | 623/1.12 |
| 2012/0083871 | A1* | 4/2012 | Ryan | 623/1.15 |

FOREIGN PATENT DOCUMENTS

| DE | 102009006180 A1 | 5/2010 |
|---|---|---|
| WO | WO 0135864 A1 | 5/2001 |

OTHER PUBLICATIONS

European Application No. 14159079.4 Search Report dated Jul. 28, 2014.

* cited by examiner

*Primary Examiner* — Randy Shay

(57) ABSTRACT

An expansion ring for a braided stent includes a plurality of elongated forked frame elements forming the expansion ring. Each of the frame elements includes first and second legs extending in one direction and connected together at a junction portion forming a fulcrum allowing compression of the frame elements, and each of the frame elements are threaded through interstices in a tubular body of the braided stent so that the junction portions engage the tubular body of the braided stent. Each of the frame elements is connected sequentially to adjacent frame elements at the ends of the first and second legs, and the expansion ring has a compressed configuration with a first diameter and an expanded configuration with a second diameter larger than the first diameter.

10 Claims, 6 Drawing Sheets

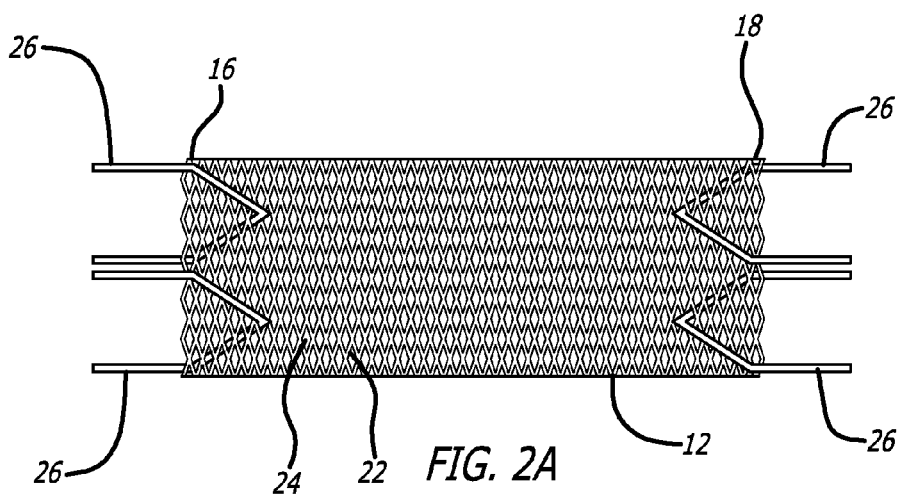
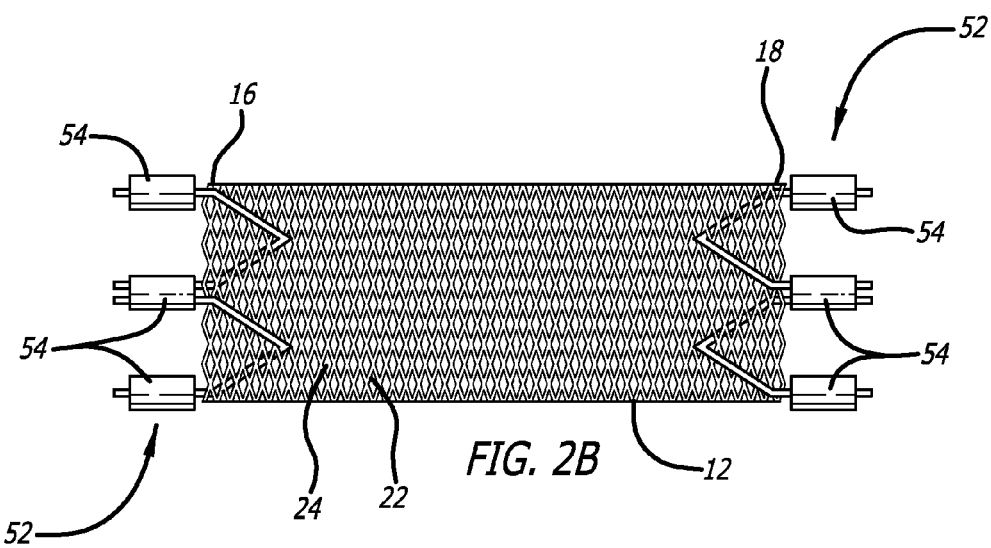
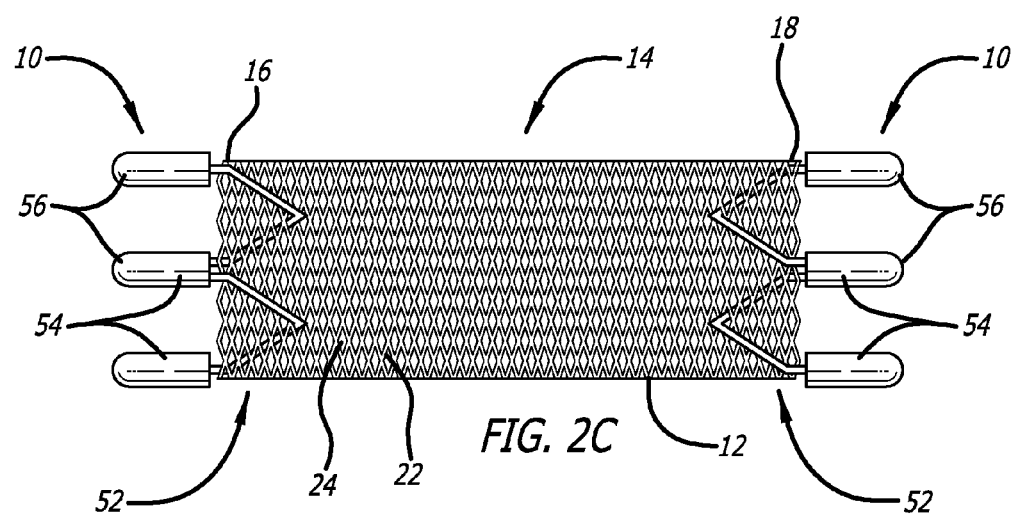

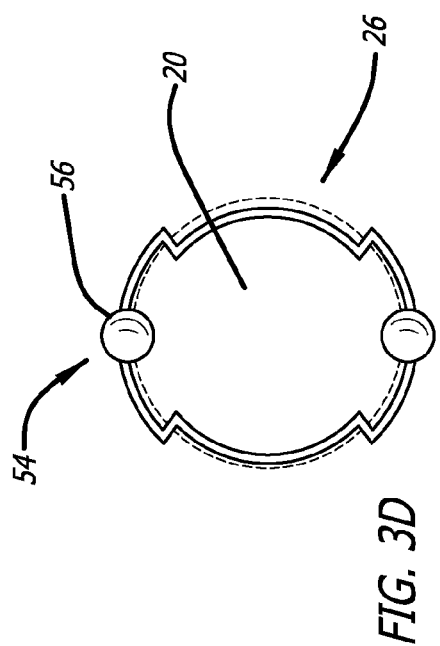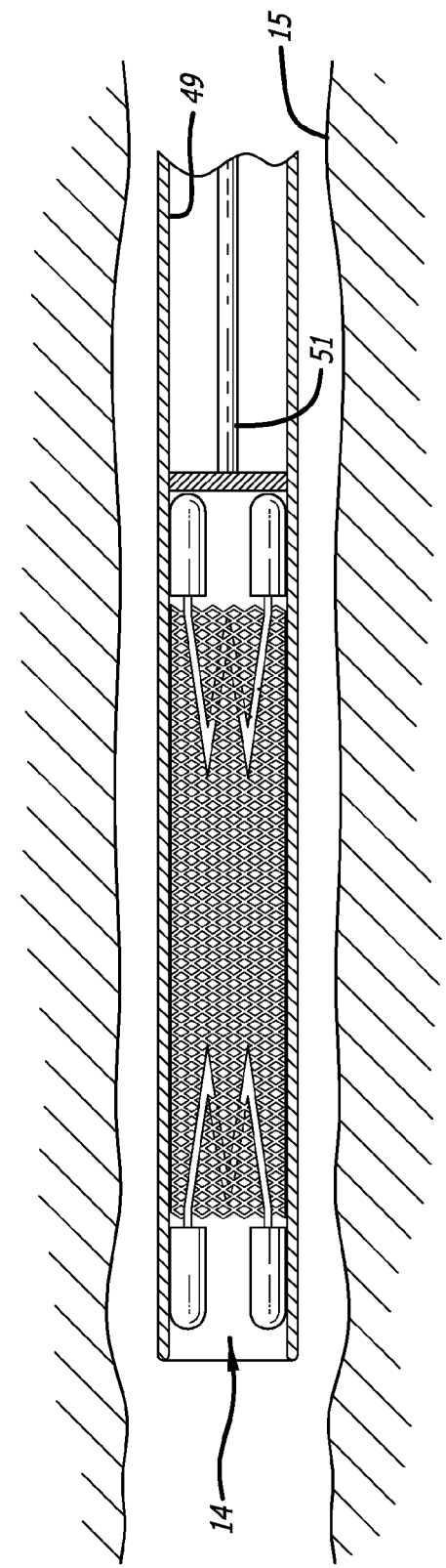

BRAID EXPANSION RING WITH MARKERS

BACKGROUND OF THE INVENTION

This invention relates generally to devices for interventional therapeutic treatment or vascular surgery for treatment of defects in the vasculature, and more particularly concerns an expansion ring for opening ends of a braided stent for treatment of vascular disease.

Stents, which are tubular reinforcements inserted into a blood vessel to provide an open path within the blood vessel, have been widely used in intravascular angioplasty treatment of occluded cardiac arteries. In such applications, the stent is inserted after an angioplasty procedure or the like in order to prevent restenosis of the artery. In these applications, the stents are often deployed by use of inflatable balloons, or mechanical devices which force the stent open, thereby reinforcing the artery wall and provide a clear through-path in the center of the artery after the angioplasty procedure to prevent restenosis.

While such procedures may be useful in certain aspects of vascular surgery in which vasoocclusive devices are used, the weakness of the vasculature and the tortuosity of the neurovasculature places limits on the applicability of such stents in procedures to repair neurovascular defects. Furthermore, the use of placement techniques, such as balloons or mechanical expansions of the type often found to be useful in cardiac surgery, are relatively less useful in vasoocclusive surgery, particularly when tiny vessels, such as those found in the brain, are to be treated. Hence, those skilled in the art have recognized a need for a stent compatible with techniques in vasoocclusive treatment of neurovascular defects that provides selective reinforcement in the vicinity of a neurovascular defect, while avoiding any unnecessary trauma or risk of rupture to the blood vessel.

Braided stents are typically formed from a plurality of elongate members, such as two or more metal wires, or polymeric fibers or strands of material, for example, and can be very useful in treatment of neurovascular defects. However, one of the problems in deploying a self-expanding braided stent in a body lumen is activation of the initially expanding end, typically the distal end of the braided stent, to fully open. It is important that the initially expanding end should open fully, easily, and quickly, so that the rest of the length of self-expanding braided stent can be deployed, using the initially expanding end as an anchor point.

Stents made of braided wire also commonly have a high internal friction that resists the inherent radial expansion force of the self-expanding braided stent to open, particularly resisting opening of the initially expanding end, which can cause problems in anchoring and deployment of such self-expanding braided stents. Current self-expanding braided stents are commonly not optimal because they depend solely on their material, dimension, cell design, and internal friction to expand. Deployment of such self-expanding braided stents commonly require extra manipulation by a user to fully open the self-expanding braided stents, which affects placement accuracy and adds risk to the procedure. The deployment and fixation of the distal end of a self-expanding braided stent is necessary for the proper alignment and positioning of the remainder of the stent body.

It would be desirable to provide an expansion ring that can be attached to an end of a braided stent to insure that the braided stent will fully expand during delivery of the braided stent to a treatment site once the braided stent is unconstrained by a delivery microcatheter. It would be desirable to provide an expansion ring with a design that simplifies the attachment of the expansion ring to a braided stent. The present invention meets these and other needs.

SUMMARY OF THE INVENTION

Briefly and in general terms, the present invention provides for an expansion ring for combination with a tubular braided stent body, that can be attached to either or both ends of a braided stent to facilitate expansion of the braided stent body upon release of the braided stent body from a microcatheter at a treatment site, and that ensures that the braided stent body will be self-expanding once it is deployed in a patient's vasculature, minimizing the potential for damage to the patient's vasculature as compared to a braided stent without such an expansion ring.

The present invention accordingly provides for an expansion ring for a braided stent, in which the expansion ring is formed from a plurality of elongated forked frame elements. Each of the plurality of elongated forked frame elements includes first and second legs having first and second terminations extending in a first direction on one side of each of the elongated forked members, and the first and second legs of each of the plurality of elongated forked frame elements are connected together at a junction portion forming one or more fulcrums therebetween allowing compression of the elongated forked frame elements at an opposing second side of each of the plurality of elongated forked frame elements, with the junction portion extending in an opposing second direction, allowing compression of the plurality of elongated forked frame elements. Each of the plurality of elongated forked frame elements is connected sequentially to adjacent ones of the plurality of elongated forked frame elements at the first and second terminations of the first and second legs to form the expansion ring. In a presently preferred aspect, the plurality of elongated forked frame elements have a compressed configuration having a first width and an expanded configuration having a second width larger than the first width.

In one presently preferred aspect, each of the plurality of elongated forked frame elements are "V" shaped, although the plurality of elongated forked frame elements alternatively be formed as "U" shaped frame elements, wherein the first and second legs of each of the plurality of elongated forked frame elements form an elliptical curve at the junction portion, or can be formed to have a "W" shape, or to have a double "U" shape, with multiple fulcrums allowing compression of the elongated forked frame elements. In another presently preferred aspect, the plurality of elongated forked frame elements are connected together in a zig-zag shaped assembly. In another presently preferred aspect, the plurality of elongated forked frame elements are formed of a superelastic material, such as a nickel titanium alloy, for example, although the plurality of elongated forked frame elements may alternatively be formed of a non-superelastic material. In another presently preferred aspect, the plurality of elongated forked frame elements may be formed of a nickel-cobalt-chromium-molybdenum alloy, or spring steel, for example. In another presently preferred aspect, the expansion ring is formed of shape memory material having a shape memory position in the expanded configuration.

In another presently preferred aspect, the first terminations are secured to adjacent second terminations of adjacent ones of the plurality of elongated forked frame elements by a plurality of metallic bands, which may be formed of a radiopaque metal, for example.

In another presently preferred aspect, the present invention provides for a braided stent, including a tubular braided stent body formed from a plurality of elongate members, with the plurality of elongate members braided to form a plurality of interstices therebetween, and at least one expansion ring connected to at least one of the proximal end and the distal end of the tubular braided stent body. Each of the plurality of elongated forked frame elements is threaded through at least one of the interstices of a portion of at least one of the proximal end and the distal end of the tubular braided stent body. In a presently preferred aspect, each of the plurality of elongated forked frame elements includes first and second legs having first and second terminations extending in a first direction on one side of each of the elongated forked elements, with the first and second legs connected together at a junction portion forming one or more fulcrums therebetween allowing compression of the elongated forked frame elements at an opposing second side of each of the elongated forked frame elements, and the junction portion extending in an opposing second direction.

Each of the first legs of the plurality of elongated forked frame elements extends inside the lumen of the tubular braided stent body, and each of the second legs of the plurality of elongated forked frame elements extends outside the lumen of the tubular braided stent body, such that the junction portions of the plurality of elongated forked frame elements engage the tubular braided stent body through the interstices of the tubular braided stent body. Each of the plurality of elongated forked frame elements is connected sequentially to adjacent ones of the plurality of elongated forked frame elements at the first and second terminations of the first and second legs to form the at least one expansion ring. *In another presently preferred aspect, the at least one expansion ring has a compressed configuration having a first diameter and an expanded configuration having a second diameter larger than the first diameter. In another presently preferred aspect, the tubular braided stent body is self-expanding.

Other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 2A is a side elevational schematic diagram of "V" shaped elongated forked frame elements inserted at the distal and proximal ends of a tubular braided stent body.

FIG. 2B is a side elevational schematic diagram similar to FIG. 2A showing metallic bands placed over the legs of the elongated forked frame elements at the distal and proximal ends of the tubular braided stent body.

FIG. 2C is a side elevational schematic diagram similar to FIG. 2B showing the metallic bands secured to the terminations of the legs of the elongated forked frame elements at the distal and proximal ends of the tubular braided stent body completing the combination of the expansion rings with the tubular braided stent body to form a stent according to the present invention.

FIG. 3D is an end view of the stent of FIG. 3C.

FIG. 3E is an elevational view similar to Figure, showing the stent in a compressed configuration in a delivery catheter.

DETAILED DESCRIPTION OF THE PREFERRED EMBODIMENTS

Figure 1A:
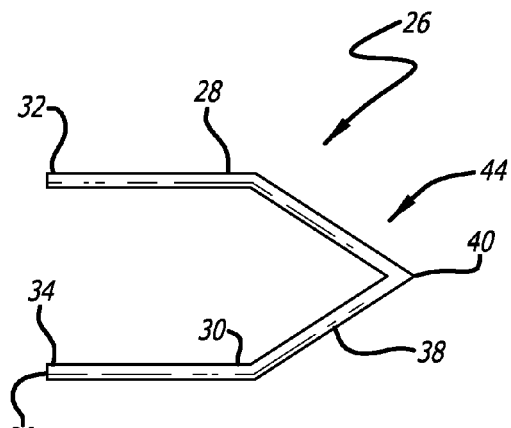
FIG. 1A is a plan view of a "V" shaped elongated forked frame element of an expansion ring according to the present invention.

Referring to the drawings, which are provided by way of example, and not by way of limitation, the present invention provides for an expansion ring 10 designed to be used in combination with a tubular braided stent body 12 to form a stent 14 for treatment of a patient's vasculature 15. The tubular braided stent body includes a proximal end 16, a distal end 18, and an inner lumen 20, and is preferably formed from a plurality of elongate members 22, braided together and forming a plurality of interstices 24 therebetween. The plurality of elongate members can include two or more metal wires, or polymeric fibers or strands of material, or combinations thereof, for example. The tubular braided stent body preferably is self-expanding, and in order to insure proper expansion and anchoring of the stent during placement of the stent, one or more expansion rings are connected to either or both of the proximal end and the distal end of the tubular braided stent body.

Each expansion ring preferably is formed from a plurality of elongated forked frame elements 26 including first legs 28 and second legs 30, having first terminations 32 and second terminations 34, respectively, extending in a first direction to one side 36 of each of the elongated forked members, with the first and second legs connected together at a junction portion 38 forming at least one fulcrum therebetween at an opposing second side 40 of each of the elongated forked members and extending generally in an opposing second direction, allowing compression of the plurality of elongated forked frame elements. As is illustrated in FIGS. 2A-3E, each of the elongated forked members preferably is threaded through interstices of a portion of the proximal end or the distal end of the tubular braided stent body, with each of the first legs of the plurality of elongated forked frame elements extending inside the lumen of the tubular braided stent body, and each of the second legs of the plurality of elongated forked frame elements extending outside the lumen of the tubular braided stent body, such that the junction portions of the plurality of elongated forked frame elements are hooked onto and engage elongate members of the tubular braided stent body through the interstices of the tubular braided stent body.

Figure 1B:
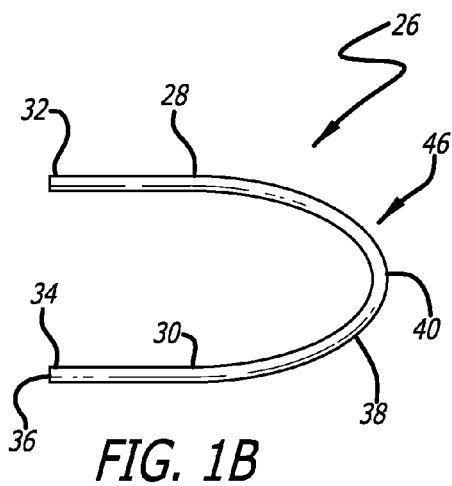
FIG. 1B is a plan view of a "U" shaped elongated forked frame element of an expansion ring according to the present invention.
Figure 1C:
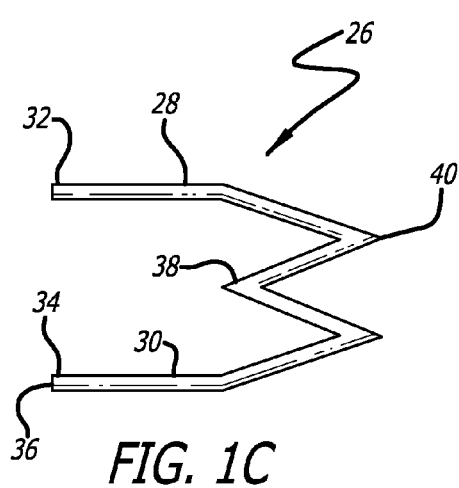
FIG. 1C is a plan view of a "W" shaped elongated forked frame element of an expansion ring according to the present invention.
Figure 1D:
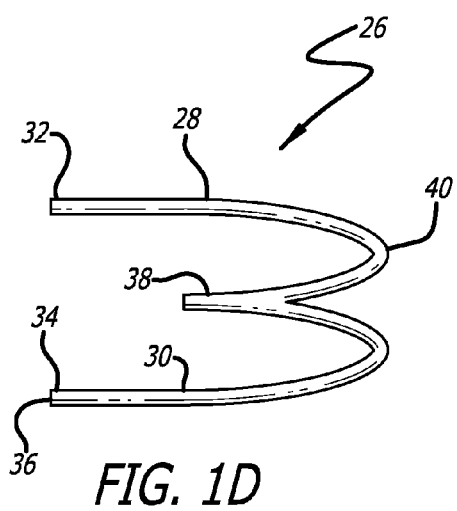
FIG. 1D is a plan view of a double "U" shaped elongated forked frame element of an expansion ring according to the present invention.
Figure 1E:
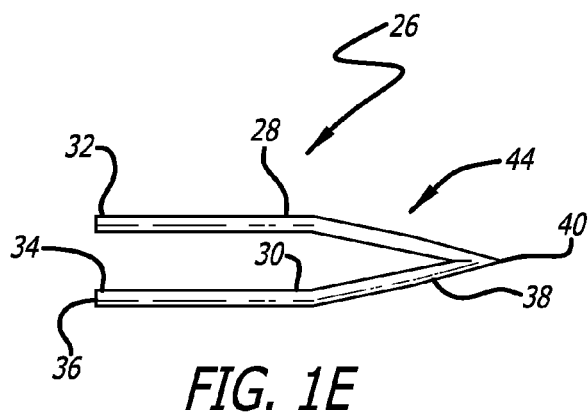
FIG. 1E is a plan view of the "V" shaped elongated forked frame element of FIG. 1A in a compressed configuration.
Figure 1F:
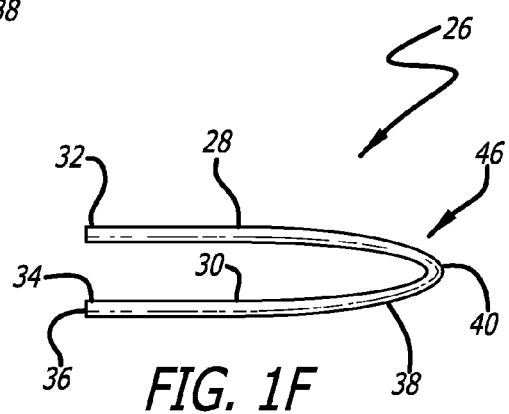
FIG. 1F is a plan view of the "U" shaped elongated forked frame element of FIG. 1B in a compressed configuration.
Figure 1G:
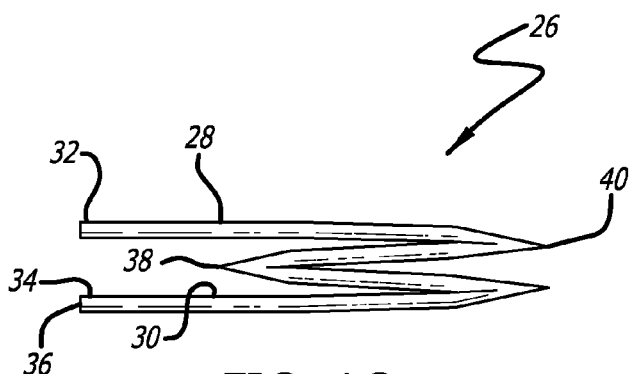
FIG. 1G is a plan view of the "W" shaped elongated forked frame element of FIG. 1C in a compressed configuration.
Figure 1H:
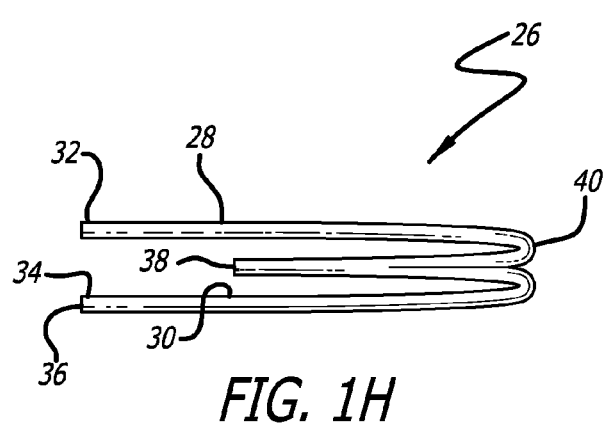
FIG. 1H a plan view of the double "U" shaped elongated forked frame element of 1D in a compressed configuration.
Figure 2D:
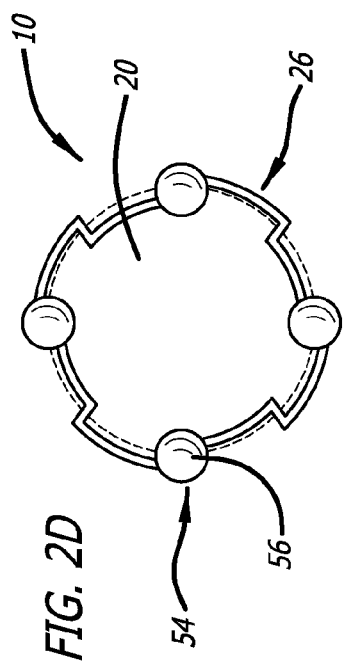
FIG. 2D is an end view of the stent of FIG. 2C.
Figure 2E:
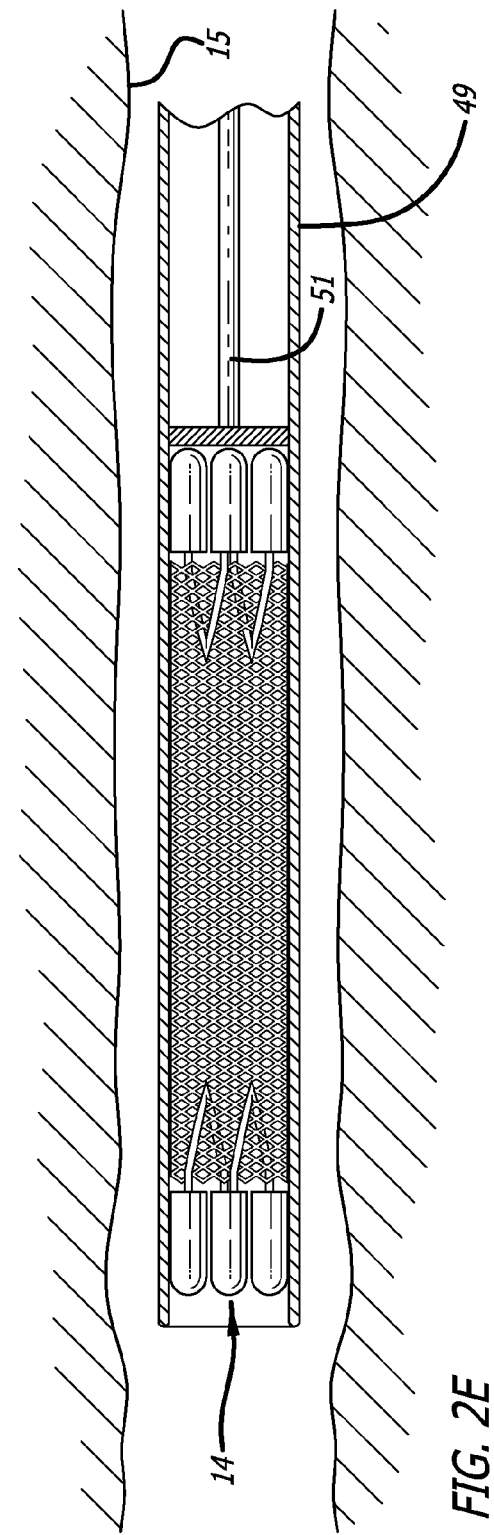
FIG. 2E is an elevational view similar to FIG. 2C, showing the stent in a compressed configuration in a delivery catheter.
Figure 3A:
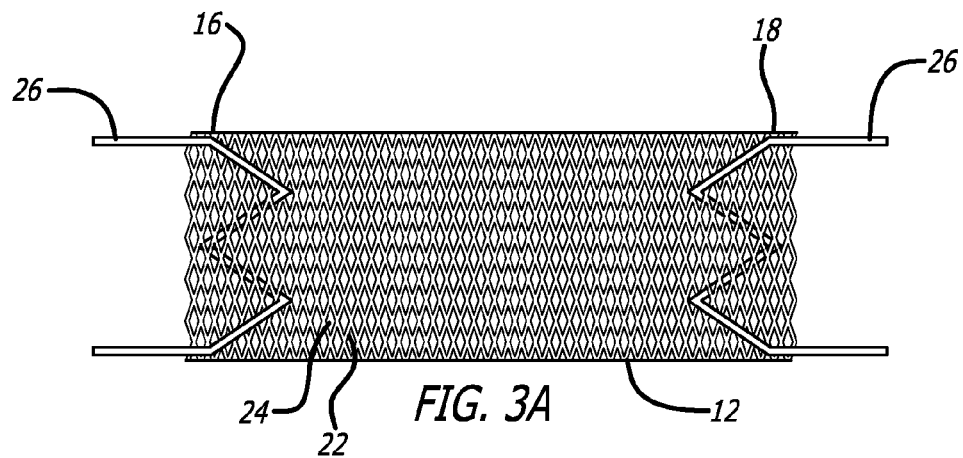
FIG. 3A is a side elevational schematic diagram of "W" shaped elongated forked frame elements inserted at the distal and proximal ends of a tubular braided stent body.
Figure 3B:
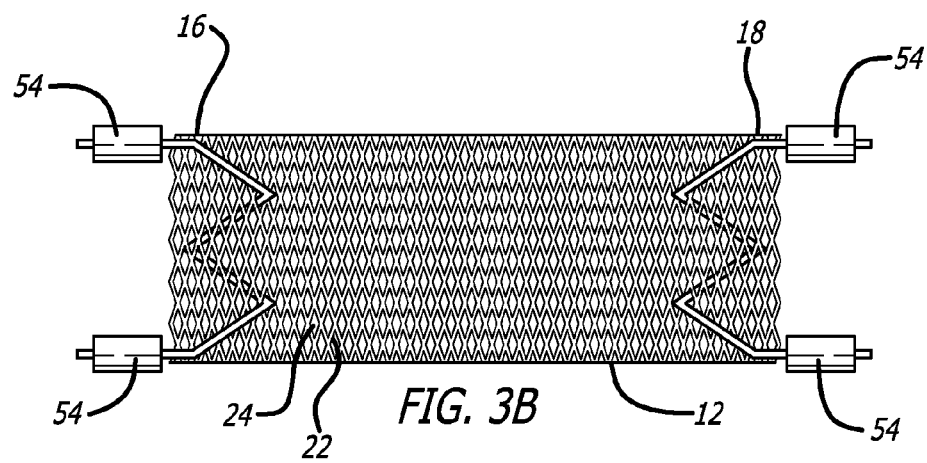
FIG. 3B is a side elevational schematic diagram similar to FIG. 3A showing metallic bands placed over the legs of the elongated forked frame elements at the distal and proximal ends of the tubular braided stent body.
Figure 3C:
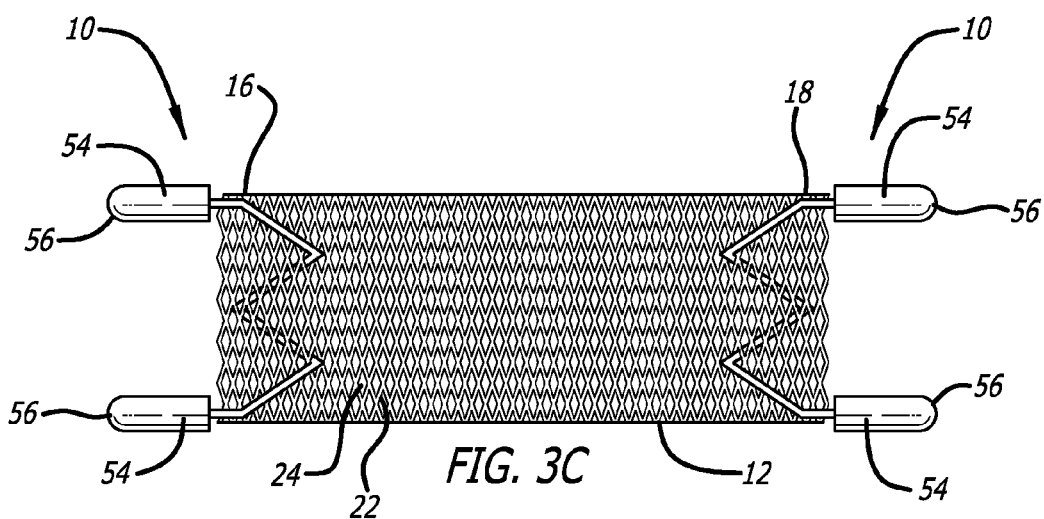
FIG. 3C is a side elevational schematic diagram similar to FIG. 3B showing the metallic bands secured to the terminations of the legs of the elongated forked frame elements at the distal and proximal ends of the tubular braided stent body completing the combination of the expansion rings with the tubular braided stent body to form a stent according to the present invention.

Referring to FIG. 1A, in a presently preferred aspect, the plurality of elongated forked frame elements can be formed as "V" shaped frame elements 44, with the legs forming a V-shaped angle at the junction portion, such as an acute angle or an oblique angle, for example, although as is shown in FIG. 1B, the plurality of elongated forked frame elements alternately can be formed as "U" shaped or elliptical shaped frame elements 46, with the legs forming a U-shaped, elliptical curve, loop or bight at the junction portion, for example. As is shown in FIG. 1C, the plurality of elongated forked frame elements can be formed as a "W" shaped elongated forked frame elements 48, with the legs forming a W-shaped formation with two V-shaped angles connected together at the junction portion, such as acute or oblique angles, for example, forming three fulcrums for compression of the frame elements, and as is shown in FIG. 1C, the plurality of elongated forked frame elements can also be formed as two connected "U" shaped elliptical shaped frame elements 50, with the legs forming a double "U" shaped formation with two connected U-shaped, elliptical curve, loop or bight portions at the junction portion, for example, forming three fulcrums for compression of the frame elements. The plurality of elongated forked frame elements preferably have an expanded configuration having a first width as is illustrated in FIGS. 1A-1D, and a compressed configuration having a second width that is smaller than the first width, as is illustrated in FIGS. 1E-1H. Consequently, the stent and expansion rings have a compressed configuration having a first diameter, illustrated in FIGS. 2E and 3E, particularly when the stent is constrained from expanding within a delivery catheter 49 for delivery through the catheter to a treatment site in a patient's vasculature, such as by an elongated pusher member 51, and the stent and expansion rings have an expanded configuration illustrated in FIGS. 2A-2C and 3A-3C, having a second diameter larger than the first diameter of the compressed configuration.

As is illustrated in FIGS. 2B-2E and 3B-3E, the plurality of elongated forked frame elements preferably are connected together sequentially to adjacent ones of the plurality of elongated forked frame elements at the first and second terminations of the first and second legs to form the expansion ring, such as in the form of a zig-zag shaped assembly 52. The plurality of elongated forked frame elements may be formed of a superelastic material, such as a nickel-titanium alloy or Nitinol, or may be formed of a non-superelastic material, such as spring steel or MP35N, an alloy of 35% nickel, 35% cobalt, 20% chromium, and 10% molybdenum, by weight, for example. The plurality of elongated forked frame elements forming the one or more expansion rings may be formed of a shape memory material having a shape memory position in the expanded configuration. The first terminations of plurality of elongated forked frame elements are preferably secured to adjacent second terminations of adjacent ones of the plurality of elongated forked frame elements, such as by metallic bands or rings 54, that are preferably welded to the terminations of the first and second legs forming caps 56 to the terminations of the legs, although the metallic bands may alternatively or additionally be secured to the terminations of the legs by soldering or crimping, for example. The metallic bands preferably are formed of a radiopaque metal, such as platinum or tantalum, although the metallic bands alternatively may be formed of a non-radiopaque material, such as stainless steel, for example.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A braided stent, comprising:
a tubular braided stent body having a proximal end, a distal end, and an inner lumen, said tubular braided stent body being formed from a plurality of elongate members, said plurality of elongate members being braided to form a plurality of interstices therebetween; and
at least one expansion ring connected to at least one of said proximal end and said distal end of said tubular braided stent body, said at least one expansion ring comprising a plurality of elongated forked frame elements, each elongated forked frame element having a fulcrum allowing compression of that elongated forked frame element, each of said plurality of elongated forked frame elements being threaded through at least one of said plurality of interstices located adjacent to a portion of said at least one of said proximal end and said distal end of said tubular braided stent body,
each of said plurality of elongated forked frame elements including first and second legs, each leg having a first free end and a second end, with said first free end of said first leg and said first free end of said second leg of a given elongated forked frame element being located, respectively, at outer edges of the elongated forked frame element, and said second end of said first leg and said second end of said second leg being connected together at a junction portion forming said fulcrum therebetween, at least a portion of each of said first legs of said plurality of elongated forked frame elements extending inside said lumen of said tubular braided stent body, and at least a portion of each of said second legs of said plurality of elongated forked frame elements extending outside said lumen of said tubular braided stent body, such that each of said plurality of elongated forked frame elements engages said tubular braided stent body through said plurality of interstices of said tubular braided stent body, and each of said plurality of elongated forked frame elements being connected sequentially to adjacent ones of said plurality of elongated forked frame elements with a first free end of a first leg of each elongated forked frame element being connected to a first free end of a second leg of an adjacent elongated forked frame element to form said at least one expansion ring, and said at least one expansion ring having a compressed configuration having a first diameter and an expanded configuration having a second diameter larger than said first diameter.

2. The braided stent of claim 1, wherein said tubular braided stent body is selfexpanding.

3. The expansion ring of claim 1, wherein each of said plurality of elongated forked frame elements have a "V" shape.

4. The expansion ring of claim 1, wherein each of said plurality of elongated forked frame elements have a "U" shape.

5. The expansion ring of claim 1, wherein each of said plurality of elongated forked frame elements have a "W" shape.

6. The expansion ring of claim 1, wherein each of said plurality of elongated forked frame elements have a double "U" shape.

7. The expansion ring of claim 1, wherein said first and second legs of each of said plurality of elongated forked frame elements form an elliptical curve at said junction portion.

8. The braided stent of claim 1, wherein said plurality of elongated forked frame elements are connected together in a zig-zag shaped assembly.

9. The braided stent of claim 1, wherein said first free ends that are connected together are connected by a metallic band.

10. The braided stent of claim 9, wherein each of said metallic bands is formed of a radiopaque metal.

* * * * *